US010980881B2

(12) United States Patent
Lee et al.

(10) Patent No.: US 10,980,881 B2
(45) Date of Patent: Apr. 20, 2021

(54) STABLE LIQUID FORMULA HAVING AN ANTI-TNFALPHA ANTIBODY, ACETATE BUFFER AND GLYCINE

(71) Applicant: CELLTRION INC., Incheon (KR)

(72) Inventors: Joon Won Lee, Incheon (KR); Yeon Kyeong Shin, Incheon (KR); Hye Young Kang, Incheon (KR); Kwang Woo Kim, Incheon (KR); So Young Kim, Incheon (KR); Su Jung Kim, Incheon (KR); Jun Seok Oh, Incheon (KR); Won Yong Han, Incheon (KR)

(73) Assignee: CELLTRION INC., Incheon (KR)

( * ) Notice: Subject to any disclaimer, the term of this patent is extended or adjusted under 35 U.S.C. 154(b) by 0 days.

(21) Appl. No.: 16/477,187

(22) PCT Filed: Jan. 10, 2018

(86) PCT No.: PCT/KR2018/000493
§ 371 (c)(1),
(2) Date: Jul. 10, 2019

(87) PCT Pub. No.: WO2018/131893
PCT Pub. Date: Jul. 19, 2018

(65) Prior Publication Data
US 2019/0343956 A1 Nov. 14, 2019

(30) Foreign Application Priority Data

Jan. 11, 2017 (KR) .................. 10-2017-0004345

(51) Int. Cl.
| | | |
|---|---|---|
| *C07K 16/24* | (2006.01) | |
| *A61K 39/395* | (2006.01) | |
| *A61K 47/12* | (2006.01) | |
| *A61K 47/18* | (2017.01) | |
| *A61K 9/08* | (2006.01) | |
| *C07K 14/525* | (2006.01) | |
| *A61K 47/26* | (2006.01) | |

(52) U.S. Cl.
CPC .......... *A61K 39/39591* (2013.01); *A61K 9/08* (2013.01); *A61K 39/3955* (2013.01); *A61K 47/12* (2013.01); *A61K 47/183* (2013.01); *A61K 47/26* (2013.01); *C07K 14/525* (2013.01); *C07K 16/241* (2013.01)

(58) Field of Classification Search
CPC ............ A61K 39/395; A61K 39/39591; A61K 47/12; A61K 47/183; C07K 14/525; C07K 16/24
See application file for complete search history.

(56) References Cited

U.S. PATENT DOCUMENTS

| | | | |
|---|---|---|---|
| 6,090,382 | A | 7/2000 | Salfeld et al. |
| 6,284,471 | B1 | 9/2001 | Le et al. |
| 8,932,591 | B2 | 1/2015 | Krause et al. |
| 10,093,728 | B2 | 10/2018 | Mendiratta et al. |
| 2010/0074903 | A1 | 3/2010 | Grauschopf et al. |
| 2013/0243764 | A1 | 9/2013 | Ellis et al. |
| 2015/0071936 | A1 | 3/2015 | Mendiratta et al. |
| 2017/0106090 | A1 | 4/2017 | Gadgil et al. |

FOREIGN PATENT DOCUMENTS

| | | |
|---|---|---|
| EP | 3 085 385 A1 | 10/2016 |
| EP | 3479819 A1 | 5/2019 |
| KR | 10-2014-0054085 A | 5/2014 |
| WO | 2013/063095 A1 | 5/2013 |
| WO | 2013/190047 A1 | 12/2013 |
| WO | 2015/151115 A1 | 10/2015 |
| WO | 2015/198240 A2 | 12/2015 |
| WO | 2016/007764 A1 | 1/2016 |
| WO | 2016/128564 A1 | 8/2016 |

OTHER PUBLICATIONS

Wang et al, 2015 (International Journal of Pharmaceutics. 490: 308-315).*
Extended European Search Report issued in corresponding application No. 18738894.7, dated Nov. 22, 2019.

* cited by examiner

*Primary Examiner* — Zachary C Howard
(74) *Attorney, Agent, or Firm* — Maschoff Brennan

(57) ABSTRACT

Disclosed is a stable liquid formulation, comprising an antibody or antigen-binding portion thereof, an acetate buffer, glycine, and a surfactant, wherein the stable liquid formulation does not comprise at least one of sugar, a sugar alcohol and a metal salt, and the stable liquid formulation is still stable even upon high antibody content, and is superior in osmolality and viscosity, and subcutaneous administration thereof is possible.

20 Claims, No Drawings
Specification includes a Sequence Listing.

STABLE LIQUID FORMULA HAVING AN ANTI-TNFALPHA ANTIBODY, ACETATE BUFFER AND GLYCINE

BACKGROUND OF THE INVENTION

1. Technical Field

The present invention relates to a stable liquid formulation.

2. Description of the Related Art

Protein formulations, particularly antibody formulations for intravenous injection, have been used for a considerable period of time. Proteins, especially antibodies, tend to form aggregates and/or dimers and become fragmented or denatured. When a formulation comprising the same is injected intravenously, serious side effects, for example, anaphylactic shock, may occur. Many attempts have been made to prevent the aggregation and fragmentation thereof and to improve the stability thereof. For example, an antibody for intravenous injection is often lyophilized to improve stability during storage thereof, but such a formulation has to be reconstituted with a diluent before use. The reconstitution process is inconvenient and time-consuming and increases the likelihood of contamination of the product.

Various liquid formulations are known as conventional formulations comprising the antibody. U.S. Pat. No. 8,932,591 discloses a stable liquid pharmaceutical formulation comprising an anti-hTNFα antibody, a polyol, a surfactant and a buffer system (citrate and phosphate). However, this formulation, having a low antibody content of about 50 mg/mL, is limited in the amount and frequency of administration, and there is still a need for improvement in terms of stability.

U.S. Publication No. 2005-0260204 discloses an antibody formulation comprising an antibody, histidine, a polyol and/or NaCl. However, this liquid formulation, comprising NaCl as a tonicity agent, may encounter problems such as precipitation and gelatinization, and there is still a need for improvement in terms of stability.

Korean Patent Application Publication No. 10-2014-0134689 discloses a liquid formulation, comprising an effective amount of an antibody or antigen-binding portion thereof directed to TNF-α in a buffer system (succinate), a surfactant, a tonicity agent (NaCl or KCl) and a stabilizer selected from among an amino acid (arginine) and cyclodextrin. However, the liquid formulation comprises NaCl or KCl as the tonicity agent, which may thus cause problems such as precipitation and gelatinization, and may be limited in the amount and frequency of administration owing to the low antibody content of about 50 mg/mL.

There is thus required a stable liquid formulation, which is able to solve the problems with the conventional liquid formulations and comprises an antibody.

SUMMARY OF THE INVENTION

Accordingly, the present invention is intended to provide a stable liquid formulation.

In addition, the present invention is intended to provide a stable liquid formulation, which is still stable even when having high antibody content.

In addition, the present invention is intended to provide a stable liquid formulation having superior osmolality and viscosity.

In addition, the present invention is intended to provide a stable liquid formulation suitable for use in subcutaneous administration.

In an embodiment of the present invention, a stable liquid formulation comprises an antibody or antigen-binding portion thereof, an acetate buffer, glycine, and a surfactant, wherein the stable liquid formulation may not comprise at least one of sugar, a sugar alcohol and a metal salt.

In an embodiment of the present invention, (A) the antibody may comprise a monoclonal antibody.

In an embodiment of the present invention, (A) the antibody may comprise a fully human antibody.

In an embodiment of the present invention, (A) the antibody may comprise an antibody binding to TNF-α.

In an embodiment of the present invention, (A) the antibody may comprise at least one of infliximab, adalimumab, certolizumab pegol and golimumab.

In an embodiment of the present invention, (A) the antibody may comprise a light-chain variable region comprising a CDR1 domain comprising the amino acid sequence of SEQ ID NO:1, a CDR2 domain comprising the amino acid sequence of SEQ ID NO:2, and a CDR3 domain comprising the amino acid sequence of SEQ ID NO:3, and a heavy-chain variable region comprising a CDR1 domain comprising the amino acid sequence of SEQ ID NO:4, a CDR2 domain comprising the amino acid sequence of SEQ ID NO:5, and a CDR3 domain comprising the amino acid sequence of SEQ ID NO:6.

In an embodiment of the present invention, (A) the antibody may comprise a light-chain variable region comprising the amino acid sequence of SEQ ID NO:7 and a heavy-chain variable region comprising the amino acid sequence of SEQ ID NO:8.

In an embodiment of the present invention, (A) the antibody may comprise a light chain comprising the amino acid sequence of SEQ ID NO:9 and a heavy chain comprising the amino acid sequence of SEQ ID NO: 10.

In an embodiment of the present invention, (A) the antibody may have a concentration of 50 to 150 mg/mL.

In an embodiment of the present invention, (B) the acetate buffer may comprise acetate.

In an embodiment of the present invention, the amount of acetate may be 1 to 30 mM.

In an embodiment of the present invention, the stable liquid formulation may not comprise at least one of histidine, citrate, phosphate, maleate, tartrate, and succinate.

In an embodiment of the present invention, (C) the glycine may have a concentration of 100 to 300 mM.

In an embodiment of the present invention, the stable liquid formulation may not comprise at least one of alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine.

In an embodiment of the present invention, (D) the surfactant may comprise polysorbate, poloxamer, or a mixture thereof.

In an embodiment of the present invention, (D) the surfactant may comprise at least one of Polysorbate 20, Polysorbate 40, Polysorbate 60, and Polysorbate 80.

In an embodiment of the present invention, (D) the surfactant may comprise Polysorbate 80.

In an embodiment of the present invention, (D) the surfactant may have a concentration of 0.01 to 1% (w/v).

In an embodiment of the present invention, the pH of the stable liquid formulation may range from 4.5 to 5.5.

In an embodiment of the present invention, the osmolality of the stable liquid formulation may range from 200 to 400 mmol/kg.

In an embodiment of the present invention, the stable liquid formulation may not comprise a preservative, a chelating agent, or a mixture thereof.

In an embodiment of the present invention, a stable liquid formulation comprises 50 to 150 mg/mL of an antibody or antigen-binding portion thereof, an acetate buffer comprising 1 to 30 mM of an acetate, 100 to 300 mM of a glycine, and 0.01 to 1% (w/v) of a surfactant, wherein the stable liquid formulation may not comprise at least one of sugar, a sugar alcohol and a metal salt.

In an embodiment of the present invention, a stable liquid formulation comprises (A) 50 to 150 mg/mL of an antibody or antigen-binding portion thereof, comprising a light-chain variable region comprising a CDR1 domain comprising the amino acid sequence of SEQ ID NO:1, a CDR2 domain comprising the amino acid sequence of SEQ ID NO:2, and a CDR3 domain comprising the amino acid sequence of SEQ ID NO:3 and a heavy-chain variable region comprising a CDR1 domain comprising the amino acid sequence of SEQ ID NO:4, a CDR2 domain comprising the amino acid sequence of SEQ ID NO:5, and a CDR3 domain comprising the amino acid sequence of SEQ ID NO:6, (B) an acetate buffer comprising 1 to 30 mM of an acetate, (C) 100 to 300 mM of a glycine, and (D) 0.01 to 1% (w/v) of a surfactant, wherein the stable liquid formulation may not comprise at least one of sugar, a sugar alcohol and a metal salt.

In an embodiment of the present invention, a stable liquid formulation comprises (A) 100 mg/mL of an antibody or antigen-binding portion thereof, comprising a light-chain variable region comprising a CDR1 domain comprising the amino acid sequence of SEQ ID NO:1, a CDR2 domain comprising the amino acid sequence of SEQ ID NO:2, and a CDR3 domain comprising the amino acid sequence of SEQ ID NO:3 and a heavy-chain variable region comprising a CDR1 domain comprising the amino acid sequence of SEQ ID NO:4, a CDR2 domain comprising the amino acid sequence of SEQ ID NO:5, and a CDR3 domain comprising the amino acid sequence of SEQ ID NO:6, (B) an acetate buffer comprising 10 mM acetate, (C) 250 mM glycine, and (D) 0.1% (w/v) of a surfactant, wherein the stable liquid formulation may not comprise at least one of sugar, a sugar alcohol and a metal salt.

In an embodiment of the present invention, the stable liquid formulation may be used for subcutaneous administration.

In another embodiment of the present invention, a pre-filled syringe filled with the stable liquid formulation is provided.

In still another embodiment of the present invention, an auto-injector comprising the pre-filled syringe therein is provided.

According to the present invention, a stable liquid formulation is still stable even upon high antibody content, can exhibit superior osmolality and viscosity, and is suitable for use in subcutaneous administration.

DESCRIPTION OF THE SPECIFIC EMBODIMENTS

[Stable Liquid Formulation]

In an embodiment of the present invention, a stable liquid formulation comprises an antibody or antigen-binding portion thereof, an acetate buffer, glycine, and a surfactant, and may not comprise at least one of sugar, a sugar alcohol and a metal salt.

"Stable" or "Stability"

As used herein, the term "stable" or "stability" means that the antibody according to the present invention substantially retains physical stability, chemical stability and/or biological activity during the preparation process thereof and/or upon the storage thereof. A variety of analytical techniques for measuring the stability of the antibody may be easily performed in the art.

Physical stability may be evaluated through any method known in the art, comprising measurement of a sample's apparent attenuation of light (absorbance or optical density). Such measurement of light attenuation is related to the turbidity of a formulation. For physical stability, a high-molecular-weight component content, a low-molecular-weight component content, an intact protein content, the number of sub-visible particles and the like may be measured.

Chemical stability may be evaluated by, for example, detecting and quantifying the antibody in a chemically modified form. Chemical stability comprises, for example, charge change that may be assessed by ion exchange chromatography (e.g. resulting from deamidation or oxidation). For chemical stability, a charge variant (acidic or basic peak) may be measured.

The biological activity may be evaluated through any method known in the art, comprising, for example, measuring antigen-binding affinity using ELISA.

As used herein, the expression "not comprise" or "without comprising" means that absolutely none of the corresponding component is comprised. Also, the above expression means that the corresponding component is not substantially comprised, that is, is comprised within a range that does not affect the activity of an antibody or the stability and viscosity of a liquid formulation, for example in an amount of 0 to 1% (w/v), 0 to 1 ppm (w/v) or 0 to 1 ppb (w/v) based on the total weight of the liquid formulation.

(A) Antibody

The antibody is an immunoglobulin molecule comprising four polypeptide chains configured such that two heavy chains and two light chains are connected to each other by means of disulfide bonds. Naturally occurring antibodies having other changed structures, for example, camelid antibodies, are also comprised in the above definition. Each heavy chain is composed of a heavy-chain variable region and a heavy-chain invariable region. The heavy-chain invariable region is composed of three domains (CH1, CH2 and CH3). Each light chain is composed of a light-chain variable region and a light-chain invariable region. The light-chain invariable region is composed of one domain (CL). The heavy-chain variable region and the light-chain variable region may be further subdivided into a hypervariable region, called a complementarity-determining region (CDR), disposed together with a more conserved region, called a framework region (FR). Each of the heavy-chain variable region and the light-chain variable region is composed of three CDRs and four FRs, which are arranged in the following sequence from the amino terminal to the carboxyl terminal: FR1, CDR1, FR2, CDR2, FR3, CDR3, FR4.

In an embodiment of the present invention, the antibody may comprise a polyclonal antibody, a monoclonal antibody, a recombinant antibody, a single-chain antibody, a hybrid antibody, a chimeric antibody, a humanized antibody, a fully human antibody or fragments thereof. In an embodiment of the present invention, the antibody may comprise a monoclonal antibody. A chimeric human-mouse monoclonal antibody may be prepared using the method known in the art. For example, infliximab may be prepared by the method disclosed in U.S. Pat. No. 6,284,471. A fully human antibody is made to reduce the side effects of a humanized antibody or a chimeric antibody, and transgenic mouse and phage display technology has been confirmed to be a successful preparation method thereof. In an embodiment of the present invention, the antibody may comprise a fully human antibody. The fully human monoclonal antibody may be prepared by a known method. For example, adalimumab may be prepared by the method disclosed in U.S. Pat. No. 6,090,382.

In an embodiment of the present invention, the antibody may comprise an antibody binding to TNF-α or an epitope of TNF-α. The antibody binding to TNF-α or the epitope of TNF-α may comprise infliximab, adalimumab, certolizumab pegol, golimumab, or mixtures thereof. In an embodiment of the present invention, the antibody may comprise adalimumab.

In an embodiment of the present invention, the antibody may comprise a light-chain variable region comprising a CDR1 domain comprising the amino acid sequence of SEQ ID NO:1, a CDR2 domain comprising the amino acid sequence of SEQ ID NO:2, and a CDR3 domain comprising the amino acid sequence of SEQ ID NO:3, and a heavy-chain variable region comprising a CDR1 domain comprising the amino acid sequence of SEQ ID NO:4, a CDR2 domain comprising the amino acid sequence of SEQ ID NO:5, and a CDR3 domain comprising the amino acid sequence of SEQ ID NO:6.

In an embodiment of the present invention, the antibody may comprise a light-chain variable region comprising the amino acid sequence of SEQ ID NO:7 and a heavy-chain variable region comprising the amino acid sequence of SEQ ID NO:8.

In an embodiment of the present invention, the antibody may comprise a light chain comprising the amino acid sequence of SEQ ID NO:9 and a heavy chain comprising the amino acid sequence of SEQ ID NO: 10.

In the present invention, the concentration of the antibody may be 50 mg/mL or more. The concentration of the antibody may be freely adjusted within a range that has substantially no adverse influence on the stability and viscosity of the stable liquid formulation according to the present invention. In an embodiment of the present invention, the concentration of the antibody may fall in the range of 50 to 150 mg/mL, for example, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150 mg/mL. In another embodiment of the present invention, the concentration of the antibody may fall in the range of 55 to 145 mg/mL, 60 to 140 mg/mL, 65 to 135 mg/mL, 70 to 130 mg/mL, 75 to 125 mg/mL, 80 to 120 mg/mL, 85 to 115 mg/mL, 90 to 110 mg/mL or 95 to 105 mg/mL. When the concentration of the antibody falls within the above range, freedom to determine the dose and frequency of administration may increase due to the high content of the antibody, and the formulation may be superior in terms of stability, viscosity and ease of preparation thereof.

(B) Acetate Buffer

The acetate buffer may comprise acetate. Examples of the acetate may comprise, but are not limited to, sodium acetate, zinc acetate, aluminum acetate, ammonium acetate, and potassium acetate. The acetate buffer may be prepared by mixing the acetate with acetic acid. In an embodiment of the present invention, the acetate buffer may comprise sodium acetate.

In an embodiment of the present invention, the stable liquid formulation may not comprise an additional buffer. In an embodiment of the present invention, the stable liquid formulation may not comprise histidine, citrate, phosphate, maleate, tartrate, succinate or mixtures thereof. When the additional buffer is comprised, in lieu of or in addition to the acetate buffer, the stability and viscosity of the formulation may deteriorate. In particular, the stability of the formulation may become poor under UV radiation or harsh conditions, and relatively severe pain may be caused upon subcutaneous injection thereof.

In an embodiment of the present invention, the amount of acetate in the acetate buffer may be freely adjusted within a range that has substantially no adverse influence on the stability, viscosity and osmolality of the liquid formulation according to the present invention. For example, the amount of acetate may fall in the range of 0.1 to 45 mM, 1 to 30 mM, 1 to 25 mM, or 5 to 15 mM, for example, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 mM. When the amount of acetate falls within the above range, the stability, osmolality and viscosity of the formulation may be superior.

Meanwhile, the amount of acetate is acetate content in the formulation stored in a single container (a vial or a pre-filled syringe). In a container for multiple distributions or multiple administrations, the amount of acetate may be increased several times depending on the number of distributions or administrations. In contrast, when a small container is used, the amount of acetate may be decreased so as to be suitable therefor.

(C) Glycine

In an embodiment of the present invention, the stable liquid formulation comprises glycine as an amino acid. Glycine may function as a stabilizer, and may contribute to adjusting the physiological osmolality. In an embodiment of the present invention, the stable liquid formulation may not comprise at least one of alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine. When an additional amino acid is comprised in lieu of or in addition to glycine, the solubility may become poor, thus making it impossible to prepare a liquid formulation or deteriorating stability.

In an embodiment of the present invention, the amount of (C) glycine may fall in the range of 100 to 300 mM, 150 to 300 mM, or 200 to 300 mM, for example, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299 or 300 mM. When the amount of glycine falls within the above range, the osmolality, stability (sub-visible particles) and viscosity of the formulation may become superior.

(D) Surfactant

Examples of the surfactant may comprise, but are not limited to, polyoxyethylene sorbitan fatty acid ester (e.g. Polysorbate), polyoxyethylene alkyl ether (e.g. Brij), alkylphenyl polyoxyethylene ether (e.g. Triton-X), a polyoxyethylene-polyoxypropylene copolymer (e.g. Poloxamer, Pluronic), and sodium dodecyl sulfate (SDS). In an embodiment of the present invention, (D) the surfactant may comprise polysorbate, poloxamer or mixtures thereof. In an embodiment of the present invention, (D) the surfactant may comprise polyoxyethylene sorbitan fatty acid ester (Polysorbate). In an embodiment of the present invention, (D) the surfactant may comprise at least one of Polysorbate 20, Polysorbate 40, Polysorbate 60, and Polysorbate 80. In an embodiment of the present invention, (D) the surfactant may comprise Polysorbate 20, Polysorbate 80 or mixtures thereof. In an embodiment of the present invention, (D) the surfactant may comprise Polysorbate 80.

In an embodiment of the present invention, the concentration of (D) the surfactant may be freely adjusted within a range that has no adverse influence on the stability and viscosity of the stable liquid formulation according to the present invention. In an embodiment of the present invention, the concentration of (D) the surfactant may fall in the range of 0.001 to 5% (w/v), 0.01 to 1% (w/v), 0.02 to 1% (w/v), or 0.05 to 0.5% (w/v), for example, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5 or 5% (w/v). When the concentration of (D) the surfactant falls within the above range, superior stability and viscosity may be exhibited.

Non-Comprised or Additional Component

In an embodiment of the present invention, the stable liquid formulation may not comprise at least one of sugar, a sugar alcohol and a metal salt.

Sugar, such as monosaccharides, disaccharides, oligosaccharides, polysaccharides or mixtures of two or more thereof, may not be comprised therein. Examples of the monosaccharides may comprise, but are not limited to, glucose, fructose, galactose, etc. Examples of the disaccharides may comprise, but are not limited to, sucrose, lactose, maltose, trehalose, etc. Examples of the oligosaccharides may comprise, but are not limited to, fructooligosaccharide, galactooligosaccharide, mannanoligosaccharide, etc. Examples of the polysaccharides may comprise, but are not limited to, starch, glycogen, cellulose, chitin, pectin, etc.

Examples of the sugar alcohol may comprise, but are not limited to, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, polyglycitol, etc.

In an embodiment of the present invention, the sugar or sugar alcohol, such as sorbitol, mannitol, trehalose, sucrose, or mixtures of two or more thereof, may not be comprised.

When the sugar or sugar alcohol is comprised, the viscosity of the liquid formulation may increase, whereby the patient may experience more severe pain during subcutaneous injection.

In an embodiment of the present invention, the metal salt, such as NaCl, KCl, NaF, KBr, NaBr, $Na_2SO_4$, NaSCN, $K_2SO_4$ or mixtures thereof, may not be comprised. When these compounds are comprised, precipitation may occur and the resulting formulation may have a gelatin shape and may exhibit poor stability.

In an embodiment of the present invention, a chelating agent (e.g. EDTA) may not be comprised. When a chelating agent is comprised, the rate of oxidation may increase.

In an embodiment of the present invention, a preservative may not be comprised. Examples of the preservative may comprise octadecyl dimethylbenzyl ammonium chloride, hexamethonium chloride, benzalkonium chloride, benzethonium chloride, phenol, butyl alcohol, benzyl alcohol, alkyl paraben, catechol, resorcinol, cyclohexanol, 3-pentanol, m-cresol, etc. When such a preservative is comprised, it may not help to improve stability.

In an embodiment of the present invention, the stable liquid formulation may further comprise an additive that is known in the art within a range that has substantially no adverse influence on the activity of an antibody and the stability and viscosity of the formulation. For example, an aqueous carrier, an antioxidant, or a mixture of two or more thereof may be further comprised. The aqueous carrier is a carrier that is pharmaceutically acceptable (safe and non-toxic upon administration to humans) and is useful for the preparation of a liquid formulation. Examples of the aqueous carrier may comprise, but are not limited to, sterile water for injection (SWFI), bacteriostatic water for injection (BWFI), a sterile saline solution, Ringer's solution, dextrose, and the like. Examples of the antioxidant may comprise, but are not limited to, ascorbic acid and the like.

pH

In an embodiment of the present invention, the pH of the stable liquid formulation may be 4.5 to 5.5, for example, 4.5, 4.6, 4.7, 4.8, 4.9, 5.0, 5.1, 5.2, 5.3, 5.4 or 5.5. In an embodiment of the present invention, the pH may be adjusted using the acetate buffer. Specifically, when the acetate buffer is comprised in a predetermined amount, a pH in the above range may be manifested even without the use of an additional pH controller. The use of the buffer comprising histidine, citrate, phosphate, maleate, tartrate, succinate or mixtures thereof may make it difficult to realize a pH in the above range. In the case where an acid or a base (e.g. sodium hydroxide) is further comprised as the additional pH controller, the stability of the antibody may deteriorate.

Osmolality

In an embodiment of the present invention, the osmolality of the stable liquid formulation may be 200 to 400 mmol/kg, 250 to 350 mmol/kg, or 270 to 330 mmol/kg, for example, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399 or 400 mmol/kg. When the osmolality falls within the above range, pain that may occur upon subcutaneous administration may be minimized. In an embodiment of the present invention, the osmolality may be adjusted using the acetate buffer and glycine. Specifically, when the acetate buffer and glycine are comprised in predetermined amounts, the osmolality in the above range may be manifested even without the use of an additional osmolality controller. In the case where NaCl is further comprised as the additional osmolality controller, precipitation may occur and the resulting formulation may have a gelatin shape and poor stability.

Viscosity

In an embodiment of the present invention, the viscosity of the stable liquid formulation, measured at room temperature (25° C.±3° C.) immediately after the preparation process or measured after storage at 5° C.±3° C. or 40° C.±2° C. for 6 weeks, may be 0.5 to 5.0 cp, for example, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0 cp. Given the above viscosity range, pain that may occur upon subcutaneous administration may be minimized, and the formulation may be easily prepared and may exhibit superior stability. When the resulting formulation is applied to a pre-filled syringe or an auto-injector, superior plunger-stopper break loose force or dynamic gliding force may result.

In an embodiment of the present invention, the term "stable" liquid formulation may refer to a liquid formulation satisfying at least one of the following criteria.

Analysis of Appearance

A liquid formulation, the clarity of which is regarded as clear upon observation after storage at a temperature of 5° C.±3° C. for 6 weeks.

A liquid formulation, the clarity of which is regarded as clear upon observation after storage at a temperature of 5° C.±3° C. for 6 weeks.

A liquid formulation, the clarity of which is regarded as clear upon observation after storage at a temperature of 40° C.±2° C. for 6 weeks.

A liquid formulation, the clarity of which is regarded as clear upon observation after storage at a temperature of 40° C.±2° C. and a relative humidity of 75±5% for 6 weeks.

Turbidity

A liquid formulation, the absorbance of which is measured to be 0 to 0.0900 at 350 nm using a spectrophotometer after storage at a temperature of 5° C.±3° C. for 6 weeks.

A liquid formulation, the absorbance of which is measured to be 0 to 0.0900 at 350 nm using a spectrophotometer after storage at a temperature of 5° C.±3° C. for 6 weeks.

A liquid formulation, the absorbance of which is measured to be 0 to 0.1300 at 350 nm using a spectrophotometer after storage at a temperature of 40° C.±2° C. for 6 weeks.

A liquid formulation, the absorbance of which is measured to be 0 to 0.1300 at 350 nm using a spectrophotometer after storage at a temperature of 40° C.±2° C. and a relative humidity of 75±5% for 6 weeks, A liquid formulation, the absorbance of which is measured to be 0 to 0.0900 at 350 nm using a spectrophotometer after storage at a temperature of 45° C.±2° C. for 3 weeks.

High-Molecular-Weight Component (a Peak in which the Retention Time Thereof is Located Before a Main Peak (Intact IgG))

A liquid formulation, the high-molecular-weight component content of which is measured to be 0 to 0.3% through size-exclusion high-performance liquid chromatography (SE-HPLC) after storage at a temperature of 5° C.±3° C. for 6 weeks.

A liquid formulation, the high-molecular-weight component content of which is measured to be 0 to 0.3% through SE-HPLC after storage at a temperature of 5° C.±3° C. for 6 weeks.

A liquid formulation, the high-molecular-weight component content of which is measured to be 0 to 0.9% through SE-HPLC after storage at a temperature of 40° C.±2° C. for 6 weeks.

A liquid formulation, the high-molecular-weight component content of which is measured to be 0 to 0.9% through SE-HPLC after storage at a temperature of 40° C.±2° C. and a relative humidity of 75±5% for 6 weeks.

A liquid formulation, the high-molecular-weight component content of which is measured to be 0 to 1.4% through SE-HPLC after storage at a temperature of 45° C.±2° C. for 3 weeks.

Main Component Content (Main Peak)

A liquid formulation, the main component content of which is measured to be 99.7% to 100% through SE-HPLC after storage at a temperature of 5° C.±3° C. for 6 weeks.

A liquid formulation, the main component content of which is measured to be 99.7% to 100% through SE-HPLC after storage at a temperature of 5° C.±3° C. for 6 weeks.

A liquid formulation, the main component content of which is measured to be 95.0% to 100% through SE-HPLC after storage at a temperature of 40° C.±2° C. for 6 weeks.

A liquid formulation, the main component content of which is measured to be 95.0% to 100% through SE-HPLC after storage at a temperature of 40° C.±2° C. and a relative humidity of 75±5% for 6 weeks.

Low-Molecular-Weight Component (a Peak in which the Retention Time Thereof is Located after a Main Peak (Intact IgG))

A liquid formulation, the low-molecular-weight component content of which is measured to be 0.0% through SE-HPLC after storage at a temperature of 5° C.±3° C. for 6 weeks.

A liquid formulation, the low-molecular-weight component content of which is measured to be 0.0% through SE-HPLC after storage at a temperature of 5° C.±3° C. for 6 weeks.

A liquid formulation, the low-molecular-weight component content of which is measured to be 0 to 4.0% through SE-HPLC after storage at a temperature of 40° C.±2° C. for 6 weeks.

A liquid formulation, the low-molecular-weight component content of which is measured to be 0 to 4.0% through SE-HPLC after storage at a temperature of 40° C.±2° C. and a relative humidity of 75±5% for 6 weeks.

Intact Immunoglobulin G Content

A liquid formulation, the intact immunoglobulin G content (intact IgG %) of which is measured to be 98.0% to 100% through non-reduced capillary electrophoresis-sodium dodecyl sulfate (NR CE-SDS) after storage at a temperature of 5° C.±3° C. for 6 weeks.

A liquid formulation, the intact immunoglobulin G content (intact IgG %) of which is measured to be 98.0% to 100% through NR CE-SDS after storage at a temperature of 5° C.±3° C. for 6 weeks.

A liquid formulation, the intact immunoglobulin G content (intact IgG %) of which is measured to be 93.1% to 100% through NR CE-SDS after storage at a temperature of 40° C.±2° C. for 6 weeks.

A liquid formulation, the intact immunoglobulin G content (intact IgG %) of which is measured to be 93.1% to 100% through NR CE-SDS after storage at a temperature of 40° C.±2° C. and a relative humidity of 75±5% for 6 weeks.

Number of Sub-Visible Particles

A liquid formulation, the number of sub-visible particles (1.00 µm≤, <100.00 µm) of which is measured to be 0 to 10,000 through micro flow imaging (MFI) after storage at a temperature of 40° C.±2° C. for 6 weeks.

A liquid formulation, the number of sub-visible particles (1.00 µm≤, <100.00 µm) of which is measured to be 0 to 10,000 through MFI after storage at a temperature of 40° C.±2° C. and a relative humidity of 75±5% for 6 weeks.

A liquid formulation, the number of sub-visible particles (1.00 µm≤, <100.00 µm) of which is measured to be 0 to 5,000 through MFI after storage at a temperature of 45° C.±2° C. for 3 weeks.

[Method of Preparing Stable Liquid Formulation]

The stable liquid formulation according to the present invention may be prepared using any known method, and the preparation thereof is not limited to specific methods. For example, the liquid formulation of the invention may be prepared by adjusting the pH of a solution comprising glycine and a surfactant with the addition of an acetate buffer and then adding the resulting mixed solution with an antibody.

In an embodiment of the present invention, upon preparation of the liquid formulation, a lyophilization process may be performed or not.

When a lyophilization process is not performed, for example, the liquid formulation of the present invention is prepared and may be placed in container immediately after processing such as sterile treatment or the like.

When a lyophilization process is performed, for example, the liquid formulation of the present invention may be prepared and lyophilized, or the liquid formulation of the present invention may be prepared, lyophilized and stored, followed by replenishing or replacing any component removed or modified through lyophilization and/or storage, thereby obtaining the liquid formulation of the present invention. Also, only components except for components that may be removed or modified through lyophilization and/or storage in the liquid formulation of the present invention may be lyophilized, or may be lyophilized and stored, after which the excepted components may be added thereto, thereby obtaining the liquid formulation of the present invention.

[Method of Using Stable Liquid Formulation]

The stable liquid formulation according to the present invention may be used for the treatment of a disease to which the corresponding antibody is targeted, for example, a disease to which the activity of TNF-α is detrimental. Examples of the disease to which the activity of TNF-α is detrimental may comprise, but are not limited to, sepsis, autoimmune disease, infectious disease, grafting, malignant cancer, lung disorders, intestinal disorders, cardiac disorders, and the like.

In an embodiment of the present invention, the disease to which the activity of TNF-α is detrimental may be selected from among rheumatoid arthritis, ankylosing spondylitis, ulcerative colitis, adult Crohn's disease, pediatric Crohn's disease, psoriasis and psoriatic arthritis.

The stable liquid formulation of the present invention may be used once or several times, or for subcutaneous self-administration.

The concentrations of the components of the liquid formulation, comprising the antibody, are as described above, and the total volume of the liquid formulation may fall in the range of 0.2 to 10.0 mL, for example, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.0 mL.

The amount and timing of administration of the liquid formulation of the invention may depend on the type of disease, the severity and progress of the disease, the patient's health and treatment regime, and the judgment of the treating doctor, and are not limited to specific values. For example, a single product or several products comprising the liquid formulation may be administered in an amount of 0.1 to 10 mg/kg (e.g. in the case of a patient having a weight of 50 kg, 5 to 500 mg of an antibody) based on the mass of the antibody, after which administration in the same or different amount may be performed weekly, every other week, every 3 weeks, every month, every 2 months, or every 3 months. Also, the amount and timing of administration of the liquid formulation may be determined with reference to an approved medicament comprising the antibody, for example, Humira label.

[Treatment Method and Stabilization Method]

The present invention addresses a method of treating a disease to which the corresponding antibody is targeted, for example, a disease to which the activity of TNF-α is detrimental, the method comprising administering, to a patient suffering from a disease to which the corresponding antibody is targeted, for example, a disease to which the activity of TNF-α is detrimental, a stable liquid formulation comprising (A) an antibody or antigen-binding portion thereof, (B) an acetate buffer, (C) glycine, and (D) a surfactant, without comprising at least one of sugar, a sugar alcohol and a metal salt.

In addition, the present invention addresses a method of stabilizing an antibody in a liquid formulation, the method comprising preparing a stable liquid formulation comprising (A) an antibody or antigen-binding portion thereof, (B) an acetate buffer, (C) glycine, and (D) a surfactant, without comprising at least one of sugar, a sugar alcohol and a metal salt.

In an embodiment for the treatment method or the stabilization method, (A) the antibody may comprise a monoclonal antibody.

In an embodiment for the treatment method or the stabilization method, (A) the antibody may comprise a fully human antibody.

In an embodiment for the treatment method or the stabilization method, (A) the antibody may comprise an antibody binding to TNF-α.

In an embodiment for the treatment method or the stabilization method, (A) the antibody may comprise at least one of infliximab, adalimumab, certolizumab pegol, and golimumab.

In an embodiment for the treatment method or the stabilization method, (A) the antibody may comprise a light-chain variable region comprising a CDR1 domain comprising the amino acid sequence of SEQ ID NO: 1, a CDR2 domain comprising the amino acid sequence of SEQ ID NO:2, and a CDR3 domain comprising the amino acid sequence of SEQ ID NO:3 and a heavy-chain variable region comprising a CDR1 domain comprising the amino acid sequence of SEQ ID NO:4, a CDR2 domain comprising the amino acid sequence of SEQ ID NO:5, and a CDR3 domain comprising the amino acid sequence of SEQ ID NO:6.

In an embodiment for the treatment method or the stabilization method, (A) the antibody may comprise a light-chain variable region comprising the amino acid sequence of SEQ ID NO:7 and a heavy-chain variable region comprising the amino acid sequence of SEQ ID NO:8.

In an embodiment for the treatment method or the stabilization method, (A) the antibody may comprise a light chain comprising the amino acid sequence of SEQ ID NO:9 and a heavy chain comprising the amino acid sequence of SEQ ID NO: 10.

In an embodiment for the treatment method or the stabilization method, (A) the antibody may have a concentration of 50 to 150 mg/mL.

In an embodiment for the treatment method or the stabilization method, (B) the acetate buffer may comprise acetate.

In an embodiment for the treatment method or the stabilization method, the amount of acetate may be 1 to 30 mM.

In an embodiment for the treatment method or the stabilization method, the stable liquid formulation may not comprise at least one of histidine, citrate, phosphate, maleate, tartrate, and succinate.

In an embodiment for the treatment method or the stabilization method, (C) glycine may have a concentration of 100 to 300 mM.

In an embodiment for the treatment method or the stabilization method, the stable liquid formulation may not comprise at least one of alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine.

In an embodiment for the treatment method or the stabilization method, (D) the surfactant may comprise polysorbate, poloxamer or a mixture thereof.

In an embodiment for the treatment method or the stabilization method, (D) the surfactant may comprise at least one of Polysorbate 20, Polysorbate 40, Polysorbate 60, and Polysorbate 80.

In an embodiment for the treatment method or the stabilization method, (D) the surfactant may comprise Polysorbate 80.

In an embodiment for the treatment method or the stabilization method, (D) the surfactant may have a concentration of 0.01 to 1% (w/v).

In an embodiment for the treatment method or the stabilization method, the stable liquid formulation may have a pH ranging from 4.5 to 5.5.

In an embodiment for the treatment method or the stabilization method, the stable liquid formulation may have an osmolality ranging from 200 to 400 mmol/kg.

In an embodiment for the treatment method or the stabilization method, the stable liquid formulation may not comprise a preservative, a chelating agent or a mixture thereof.

In an embodiment for the treatment method or the stabilization method, the stable liquid formulation may further comprise an aqueous carrier, an antioxidant, or a mixture of two or more thereof.

In an embodiment for the treatment method or the stabilization method, the stable liquid formulation may have a viscosity ranging from 0.5 to 5.0 cp.

In an embodiment for the treatment method or the stabilization method, the stable liquid formulation may be used for subcutaneous administration.

[Product]

The present invention addresses a product comprising the stable liquid formulation and a container that accommodates the stable pharmaceutical formulation in a closed state.

The stable liquid formulation is described as above.

In an embodiment of the present invention, the container may be formed of glass, a polymer (plastic), a metal, or the like, but is not limited thereto. In an embodiment of the present invention, the container is a bottle, a vial, a syringe, for example a pre-fillable or pre-filled syringe, or a tube, but is not limited thereto. In an embodiment of the present invention, the container may be a vial made of glass or polymer, or a pre-filled syringe made of glass or polymer. In an embodiment of the present invention, a pre-filled syringe filled with the stable liquid formulation is provided.

In an embodiment of the present invention, the inner surface of the pre-filled syringe may be coated with silicone oil. In this case, superior plunger-stopper break loose force or dynamic gliding force may be exhibited. In an embodiment of the present invention, the inner surface of the pre-filled syringe may not be coated with silicone oil. In this case, the stability of the formulation may be superior. The container may be a single-dose or multi-dose container.

In an embodiment of the present invention, the product may be an auto-injector, and the auto-injector may comprise therein a pre-filled syringe filled with the stable liquid formulation. The auto-injector may comprise, for example, a cylindrical housing that accommodates the pre-filled syringe and an actuator (e.g. a spring) that initiates administration by applying pressure to the stopper of the pre-filled syringe, and may be formed of glass, a polymer (plastic), or metal. As the auto-injector, any one of known products may be used, or a product comprising the pre-filled syringe may be customized.

In an embodiment of the present invention, the product may further comprise instructions for either or both of the method of using the stable liquid formulation and the method of storing the stable liquid formulation. In an embodiment of the present invention, the usage method comprises a cure for a disease to which the corresponding antibody is targeted, for example, a disease to which the activity of TNF-α is detrimental, and may comprise an administration route, dose, and timing.

In an embodiment of the present invention, the product may comprise other tools necessary from the viewpoint of a commercial purpose and a user, for example, a needle, an injector, and the like.

A better understanding of the present invention will be given through the following examples, which are merely set forth to illustrate, but are not to be construed as limiting the scope of the present invention.

EXAMPLES

With regard to the antibodies used in Examples 1 and 2 and Comparative Examples 1 to 5 and 7 to 12, adalimumab, made by Celltrion, was used, and with regard to the antibody used in Comparative Example 6, adalimumab (Humira®), made by AbbVie was used.

In order to measure the physical and chemical stability of the liquid formulations of Examples, the following methods were used.

Analysis of Appearance

The clarity of the formulation was observed.

Turbidity

The absorbance was measured at 350 nm using a UV-Vis spectrophotometer.

Main Component Content

The main component content (main peak; %) was measured using size-exclusion high-performance liquid chromatography (SE-HPLC).

High-Molecular-Weight Component Content

The high-molecular-weight component content (pre-peak; %) was measured using SE-HPLC.

Low-Molecular-Weight Component Content

The low-molecular-weight component content (post-peak; %) was measured using SE-HPLC.

Intact Immunoglobulin G Content (Intact IgG %)

The intact immunoglobulin G content (%) was measured using non-reduced capillary electrophoresis-sodium dodecyl sulfate (NR CE-SDS).

Number of Sub-Visible Particles

The number of sub-visible particles (1.00 μm≤, <100.00 μm) was measured using micro flow imaging (MFI).

Osmolality

The osmolality (mmol/kg) was measured using an osmometer (VAPRO 5520).

Viscosity

The viscosity in a 500 μL syringe was measured at 25° C.±0.1° C. using a micro-capillary rheometer (apparent shear rate: 103~105 s-1) equipped with a flow cell (B05 sensor type, 50 μm cell depth).

Examples 1 and 2 and Comparative Examples 1 to 12

In the liquid formulations of Examples 1 and 2 and Comparative Examples 1 to 12, each buffer was prepared so as to be adapted for the corresponding pH, added with amino acid or a metal salt or sugar or a sugar alcohol, further added with an antibody, and furthermore added with a surfactant, thus yielding the samples set forth in Table 1 below. The specific amounts of the individual components are shown in Table 1 below. The total volume was 3 mL.

TABLE 1

| No. | Antibody content (mg/mL) | Surfactant | Amino acid or metal salt or sugar or sugar alcohol | Buffer | pH |
|---|---|---|---|---|---|
| Example 1 | 100 | Polysorbate 80 0.1% (w/v) | Glycine 250 mM | Sodium acetate 10 mM | 5.2 |
| Example 2 | 100 | Polysorbate 80 0.1% (w/v) | Glycine 280 mM | Sodium acetate 10 mM | 5.2 |
| Comparative Example 1 | 100 | Polysorbate 80 0.1% (w/v) | NaCl 30 mM, Mannitol 5% (w/v) | — | 5.2 |
| Comparative Example 2 | 100 | Polysorbate 80 0.1% (w/v) | NaCl 30 mM, Sorbitol 5% (w/v) | — | 5.2 |
| Comparative Example 3 | 100 | Polysorbate 80 0.1% (w/v) | NaCl 30 mM, Trehalose 8% (w/v) | — | 5.2 |
| Comparative Example 4 | 100 | Polysorbate 80 0.1% (w/v) | NaCl 30 mM, Sucrose 8% (w/v) | — | 5.2 |
| Comparative Example 5 | 100 | Polysorbate 80 0.1% (w/v) | Lysine 250 mM | Sodium acetate 10 mM | 5.2 |
| Comparative Example 6 | 50 | Polysorbate 80 0.1% (w/v) | NaCl 105 mM Mannitol 1.2% (w/v) | Sodium phosphate 14.1 mM Sodium citrate 7.2 mM | 5.2 |
| Comparative Example 7 | 100 | Polysorbate 80 0.1% (w/v) | Glycine 310 mM | Sodium acetate 10 mM | 5.2 |
| Comparative Example 8 | 100 | Polysorbate 80 0.1% (w/v) | Glycine 250 mM | Sodium citrate 10 mM | 5.2 |
| Comparative Example 9 | 100 | Polysorbate 80 0.1% (w/v) | Glycine 250 mM | Sodium succinate 10 mM | 5.2 |
| Comparative Example 10 | 100 | Polysorbate 80 0.1% (w/v) | Glycine 90 mM | Sodium acetate 10 mM | 5.2 |
| Comparative Example 11 | 100 | Polysorbate 80 0.1% (w/v) | Glycine 250 mM | Sodium acetate 30 mM | 5.2 |
| Comparative Example 12 | 100 | Polysorbate 80 0.1% (w/v) | Glycine 250 mM | Sodium acetate 50 mM | 5.2 |

The liquid formulations of Examples 1 and 2 and Comparative Examples 1 to 7 were stored at a temperature of 5±3° C., a temperature of 40±2° C. and a relative humidity of 75±5% for 6 weeks.

Also, the liquid formulations of Example 1 and Comparative Examples 8 to 12 were stored at a temperature of 45±2° C. for 3 weeks.

Analysis of Appearance

TABLE 2

| No. | After 0 weeks at 5 ± 3° C. | After 6 weeks at 5 ± 3° C. | After 6 weeks at 40 ± 2° C. |
|---|---|---|---|
| Example 1 | Clear | Clear | Clear |
| Example 2 | Clear | Clear | Clear |
| Comparative Example 1 | Very slightly opalescent | Very slightly opalescent | Very slightly opalescent |
| Comparative Example 2 | Very slightly opalescent | Very slightly opalescent | Very slightly opalescent |
| Comparative Example 3 | Very slightly opalescent | Very slightly opalescent | Very slightly opalescent |
| Comparative Example 4 | Very slightly opalescent | Very slightly opalescent | Very slightly opalescent |
| Comparative Example 5 | Slightly opalescent | Slightly opalescent | Slightly opalescent |

Referring to Table 2, the liquid formulations of Examples 1 and 2 exhibited relatively clear from the point of time of preparation thereof compared to Comparative Examples 1 to 5, and changes in appearance over time under individual storage conditions were not observed.

Turbidity

TABLE 3

| No. | After 0 weeks at 5 ± 3° C. | After 6 weeks at 5 ± 3° C. | After 6 weeks at 40 ± 2° C. |
|---|---|---|---|
| Example 1 | 0.0845 | 0.0814 | 0.1245 |
| Example 2 | 0.1086 | 0.0650 | 0.1100 |
| Comparative Example 1 | 0.1120 | 0.1113 | 0.1364 |
| Comparative Example 2 | 0.1160 | 0.1087 | 0.1375 |
| Comparative Example 3 | 0.1115 | 0.1049 | 0.1349 |
| Comparative Example 4 | 0.1135 | 0.1070 | 0.1406 |
| Comparative Example 5 | 0.1920 | 0.1916 | 0.2385 |
| Comparative Example 6 | 0.1230 | N/A | 0.1373 |

Referring to Table 3, Examples 1 and 2, comprising the acetate buffer and glycine, were the most excellent in turbidity, and the absorbance thereof was remained low even after 6 weeks at 40° C. compared to Comparative Examples 1 to 6.

TABLE 4

| No. | After 0 weeks at 45 ± 2° C. | After 3 weeks at 45 ± 2° C. |
|---|---|---|
| Example 1 | 0.0718 | 0.1722 |
| Comparative Example 8 | 0.1439 | 0.5250 |
| Comparative Example 9 | 0.0922 | 0.2127 |
| Comparative Example 10 | 0.0719 | 0.1933 |
| Comparative Example 11 | 0.0937 | 0.2548 |
| Comparative Example 12 | 0.1096 | 0.5384 |

Referring to Table 4, Example 1, comprising 10 mM acetate buffer and 250 mM glycine, was the most excellent in turbidity, and in particular, the absorbance thereof was 0.1800 or less even after 3 weeks at 45° C., and thus remained low compared to Comparative Examples 8 to 12.

High-Molecular-Weight Component Content

TABLE 5

| No. | After 0 weeks at 5 ± 3° C. | After 6 weeks at 5 ± 3° C. | After 6 weeks at 40 ± 2° C. |
|---|---|---|---|
| Example 1 | 0.2 | 0.3 | 0.9 |
| Comparative Example 1 | 0.4 | 0.4 | 1.0 |
| Comparative Example 2 | 0.3 | 0.4 | 1.0 |
| Comparative Example 3 | 0.4 | 0.4 | 1.0 |
| Comparative Example 4 | 0.4 | 0.4 | 1.1 |

Referring to Table 5, the high-molecular-weight component content of Example 1 was the lowest under all conditions. In particular, the high-molecular-weight component content of Example 1 was less than 1.0% after 6 weeks at 40° C.

TABLE 6

| No. | After 0 weeks at 45 ± 2° C. | After 3 weeks at 45 ± 2° C. |
|---|---|---|
| Example 1 | 0.1 | 1.3 |
| Comparative Example 8 | 0.1 | 1.3 |

TABLE 6-continued

| No. | After 0 weeks at 45 ± 2° C. | After 3 weeks at 45 ± 2° C. |
|---|---|---|
| Comparative Example 9 | 0.1 | 1.7 |
| Comparative Example 10 | 0.1 | 1.3 |
| Comparative Example 11 | 0.1 | 1.6 |
| Comparative Example 12 | 0.1 | 1.8 |

Referring to Table 6, the high-molecular-weight component content of Example 1 was less than 1.5% after 3 weeks at 45° C.

Main Component Content

TABLE 7

| No. | After 0 weeks at 5 ± 3° C. | After 6 weeks at 5 ± 3° C. | After 6 weeks at 40 ± 2° C. |
|---|---|---|---|
| Example 1 | 99.7 | 99.7 | 95.3 |
| Comparative Example 1 | 99.6 | 99.6 | 94.8 |
| Comparative Example 2 | 99.6 | 99.6 | 94.7 |
| Comparative Example 3 | 99.6 | 99.6 | 94.7 |
| Comparative Example 4 | 99.6 | 99.6 | 94.7 |
| Comparative Example 5 | 99.7 | 99.7 | 94.7 |
| Comparative Example 6 | 99.6 | N/A | 94.6 |

Referring to Table 7, the monomer content of Example 1 was 95.0% or more after 6 weeks at 40° C., which was higher than in Comparative Examples 1 to 6.

TABLE 8

| No. | After 0 weeks at 45 ± 2° C. | After 3 weeks at 45 ± 2° C. |
|---|---|---|
| Example 1 | 99.4 | 95.0 |
| Comparative Example 8 | 99.4 | 95.3 |
| Comparative Example 9 | 99.4 | 95.1 |
| Comparative Example 10 | 99.4 | 95.1 |
| Comparative Example 11 | 99.4 | 94.9 |
| Comparative Example 12 | 99.4 | 94.7 |

Referring to Table 8, the monomer content of Example 1 was 95.0% or more after 3 weeks at 45° C., which was higher than in Comparative Examples 11 and 12.

Low-Molecular-Weight Component Content

TABLE 9

| No. | After 0 weeks at 5 ± 3° C. | After 6 weeks at 5 ± 3° C. | After 6 weeks at 40 ± 2° C. |
|---|---|---|---|
| Example 1 | 0.0 | 0.0 | 3.8 |
| Comparative Example 1 | 0.0 | 0.0 | 4.2 |
| Comparative Example 2 | 0.0 | 0.1 | 4.3 |
| Comparative Example 3 | 0.0 | 0.1 | 4.3 |
| Comparative Example 4 | 0.0 | 0.0 | 4.2 |
| Comparative Example 5 | 0.0 | 0.1 | 4.5 |
| Comparative Example 6 | 0.2 | N/A | 4.8 |

Referring to Table 9, the low-molecular-weight component content of Example 1 was less than 4% after 6 weeks at 40° C., which was lower than in Comparative Examples 1 to 6.

Intact Immunoglobulin G Content (Intact IgG %)

TABLE 10

| No. | After 0 weeks at 5 ± 3° C. | After 6 weeks at 5 ± 3° C. | After 6 weeks at 40 ± 2° C. |
|---|---|---|---|
| Example 1 | 98.14 | 98.10 | 93.14 |
| Comparative Example 1 | 98.14 | 98.14 | 93.07 |
| Comparative Example 2 | 98.27 | 97.92 | 92.73 |
| Comparative Example 3 | 98.15 | 97.99 | 92.78 |
| Comparative Example 4 | 98.17 | 97.94 | 92.99 |
| Comparative Example 5 | 98.15 | 97.97 | 92.69 |
| Comparative Example 6 | 98.15 | N/A | 91.25 |

Referring to Table 10, the intact IgG % of Example 1 was 93.10% or more after 6 weeks at 40° C., which was higher than in Comparative Examples 1 to 6.

Number of Sub-Visible Particles (1.00 μm≤, <100.00 μm)

TABLE 11

| No. | After 0 weeks at 5 ± 3° C. | After 6 weeks at 5 ± 3° C. | After 6 weeks at 40 ± 2° C. |
|---|---|---|---|
| Example 1 | 721 | 2881 | 4973 |
| Example 2 | 8888 | 3101 | 7115 |
| Comparative Example 6 | 41825 | N/A | 51914 |
| Comparative Example 7 | 3319 | 2864 | 37751 |

Referring to Table 11, in Example 1 or 2, in which 250 or 280 mM glycine was used, the number of sub-visible particles after 6 weeks at 40° C. was 10,000 or less. However, in Comparative Example 6 in the form of the Humira formulation, the number of sub-visible particles after 6 weeks at 40° C. was 50,000 or more. Also, in Comparative Example 7 using 310 mM glycine, the number of sub-visible particles after 6 weeks at 40° C. was 35,000 or more.

TABLE 12

| No. | After 0 weeks at 45 ± 2° C. | After 3 weeks at 45 ± 2° C. |
|---|---|---|
| Example 1 | 2560 | 4778 |
| Comparative Example 8 | 7146 | 4834586 |
| Comparative Example 9 | 655 | 5415 |
| Comparative Example 10 | 223 | 1615 |
| Comparative Example 11 | 526 | 1911 |
| Comparative Example 12 | 340 | 4332120 |

Referring to Table 12, in Example 1 using 250 mM glycine, the number of sub-visible particles after 3 weeks at 45° C. was 5000 or less. However, in Comparative Examples 8 and 12, the number of sub-visible particles after 3 weeks at 45° C. was 4,000,000 or more.

Osmolality

TABLE 13

| No. | After 0 weeks at 45 ± 2° C. | After 3 weeks at 45 ± 2° C. |
|---|---|---|
| Example 1 | 269 | 304 |
| Comparative Example 8 | 282 | 312 |
| Comparative Example 9 | 275 | 295 |
| Comparative Example 10 | 105 | 125 |
| Comparative Example 11 | 300 | 335 |
| Comparative Example 12 | 340 | 378 |

Referring to Table 13, the osmolality of Comparative Example 10 was less than 200 mmol/kg, which was lower than in Example 1 and Comparative Examples 8, 9, 11 and 12.

Viscosity

TABLE 14

| No. | After 0 weeks at 45 ± 2° C. | After 3 weeks at 45 ± 2° C. |
|---|---|---|
| Example 1 | 2.6 | 2.6 |

Referring to Table 14, the viscosity of Example 1 was measured to be less than 3.0 after 3 weeks at 45° C.

What is claimed is:

1. A liquid formulation, comprising:
   (A) an antibody or antigen-binding portion thereof;
   (B) an acetate buffer;
   (C) glycine; and
   (D) a surfactant,
   wherein:
      the liquid formulation does not comprise sucrose nor trehalose nor mannitol nor sorbitol nor NaCl,
      (A) the antibody comprises an antibody binding to TNF-α,
      (C) the glycine has a concentration of 210 to 300 mM, and
      the liquid formulation has an osmolality ranging from 200 to 400 mmol/kg.

2. The liquid formulation of claim 1, wherein (A) the antibody comprises at least one of infliximab, adalimumab, certolizumab pegol and golimumab.

3. The liquid formulation of claim 1, wherein (A) the antibody comprises:
   a light-chain variable region comprising a CDR1 domain comprising an amino acid sequence of SEQ ID NO:1, a CDR2 domain comprising an amino acid sequence of SEQ ID NO:2, and a CDR3 domain comprising an amino acid sequence of SEQ ID NO:3;
   a heavy-chain variable region comprising a CDR1 domain comprising an amino acid sequence of SEQ ID NO:4, a CDR2 domain comprising an amino acid sequence of SEQ ID NO:5, and a CDR3 domain comprising an amino acid sequence of SEQ ID NO:6,
   a light-chain variable region comprising an amino acid sequence of SEQ ID NO:7 and a heavy-chain variable region comprising an amino acid sequence of SEQ ID NO:8; and p1 a light chain comprising an amino acid sequence of SEQ ID NO:9 and a heavy chain comprising an amino acid sequence of SEQ ID NO: 10.

4. The liquid formulation of claim 1, wherein (A) the antibody has a concentration of 50 to 150 mg/mL.

5. The liquid formulation of claim 1, wherein (B) the acetate buffer has an acetate concentration of 1 to 30 mM.

6. The liquid formulation of claim 1, wherein the liquid formulation does not comprise at least one of histidine, citrate, phosphate, maleate, tartrate, and succinate.

7. The liquid formulation of claim 1, wherein the liquid formulation does not comprise at least one of alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine.

8. The liquid formulation of claim 1, wherein (D) the surfactant comprises polysorbate, poloxamer or a mixture thereof.

9. The liquid formulation of claim 1, wherein (D) the surfactant comprises at least one of Polysorbate 20, Polysorbate 40, Polysorbate 60, and Polysorbate 80.

10. The liquid formulation of claim 1, wherein (D) the surfactant has a concentration of 0.01 to 1% (w/v).

11. The liquid formulation of claim 1, having a pH ranging from 4.5 to 5.5.

12. The liquid formulation of claim 1, wherein the liquid formulation does not comprise a preservative, a chelating agent or a mixture thereof.

13. The liquid formulation of claim 1, comprising:
(A) 50 to 150 mg/mL of an antibody or antigen-binding portion thereof;
(B) an acetate buffer comprising 1 to 30 mM of an acetate;
(C) 210 to 300 mM of a glycine; and
(D) 0.01 to 1% (w/v) of a surfactant,
wherein the liquid formulation does not comprise sucrose nor trehalose nor mannitol nor sorbitol nor NaCl.

14. The stable liquid formulation of claim 1, comprising:
(A) 50 to 150 mg/mL of an antibody or antigen-binding portion thereof, comprising a light-chain variable region comprising a CDR1 domain comprising an amino acid sequence of SEQ ID NO:1, a CDR2 domain comprising an amino acid sequence of SEQ ID NO:2, and a CDR3 domain comprising an amino acid sequence of SEQ ID NO:3 and a heavy-chain variable region comprising a CDR1 domain comprising an amino acid sequence of SEQ ID NO:4, a CDR2 domain comprising an amino acid sequence of SEQ ID NO:5, and a CDR3 domain comprising an amino acid sequence of SEQ ID NO:6;
(B) an acetate buffer comprising 1 to 30 mM of an acetate;
(C) 210 to 300 mM of a glycine; and
(D) 0.01 to 1% (w/v) of a surfactant,
wherein the liquid formulation does not comprise sucrose nor trehalose nor mannitol nor sorbitol nor NaCl.

15. The liquid formulation of claim 1, comprising:
(A) 100 mg/mL of an antibody or antigen-binding portion thereof, comprising a light-chain variable region comprising a CDR1 domain comprising an amino acid sequence of SEQ ID NO:1, a CDR2 domain comprising an amino acid sequence of SEQ ID NO:2, and a CDR3 domain comprising an amino acid sequence of SEQ ID NO:3 and a heavy-chain variable region comprising a CDR1 domain comprising an amino acid sequence of SEQ ID NO:4, a CDR2 domain comprising an amino acid sequence of SEQ ID NO:5, and a CDR3 domain comprising an amino acid sequence of SEQ ID NO:6;
(B) an acetate buffer comprising 10 mM acetate;
(C) 250 mM glycine; and
(D) 0.1% (w/v) of a surfactant,
wherein the liquid formulation does not comprise sucrose nor trehalose nor mannitol nor sorbitol nor NaCl.

16. The liquid formulation of claim 1, for use in subcutaneous administration.

17. A pre-filled syringe, filled with the liquid formulation of claim 1.

18. An auto-injector, comprising therein the pre-filled syringe of claim 7.

19. A method for administration of the liquid formulation of claim 1, comprising administering to a subject the liquid formulation by subcutaneous administration.

20. A method of manufacturing the liquid formulation of claim 1, comprising:
combining the antibody or antigen-binding portion thereof with the acetate buffer, glycine and surfactant to provide the liquid formulation.

* * * * *

SEQUENCE LISTING

<160> NUMBER OF SEQ ID NOS: 10

<210> SEQ ID NO 1
<211> LENGTH: 11
<212> TYPE: PRT
<213> ORGANISM: Artificial Sequence
<220> FEATURE:
<223> OTHER INFORMATION: Antibody

<400> SEQUENCE: 1

Arg Ala Ser Gln Gly Ile Arg Asn Tyr Leu Ala
1               5                   10

<210> SEQ ID NO 2
<211> LENGTH: 7
<212> TYPE: PRT
<213> ORGANISM: Artificial Sequence
<220> FEATURE:

<223> OTHER INFORMATION: Antibody

<400> SEQUENCE: 2

Ala Ala Ser Thr Leu Gln Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Antibody

<400> SEQUENCE: 3

Gln Arg Tyr Asn Arg Ala Pro Tyr Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Antibody

<400> SEQUENCE: 4

Asp Tyr Ala Met His
1               5

<210> SEQ ID NO 5
<211> LENGTH: 17
<212> TYPE: PRT
<213> ORGANISM: Artificial Sequence
<220> FEATURE:
<223> OTHER INFORMATION: Antibody

<400> SEQUENCE: 5

Ala Ile Thr Trp Asn Ser Gly His Ile Asp Tyr Ala Asp Ser Val Glu
1               5                   10                  15

Gly

<210> SEQ ID NO 6
<211> LENGTH: 12
<212> TYPE: PRT
<213> ORGANISM: Artificial Sequence
<220> FEATURE:
<223> OTHER INFORMATION: Antibody

<400> SEQUENCE: 6

Val Ser Tyr Leu Ser Thr Ala Ser Ser Leu Asp Tyr
1               5                   10

<210> SEQ ID NO 7
<211> LENGTH: 107
<212> TYPE: PRT
<213> ORGANISM: Artificial Sequence
<220> FEATURE:
<223> OTHER INFORMATION: Antibody

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys
            100                 105

<210> SEQ ID NO 8
<211> LENGTH: 120
<212> TYPE: PRT
<213> ORGANISM: Artificial Sequence
<220> FEATURE:
<223> OTHER INFORMATION: Antibody

<400> SEQUENCE: 8

Val Gln Leu Val Glu Ser Gly Gly Leu Val Gln Pro Gly Arg Ser
 1               5                  10                  15

Leu Arg Leu Ser Cys Ala Ala Ser Gly Phe Thr Phe Asp Asp Tyr Ala
                 20                  25                  30

Met His Trp Val Arg Gln Ala Pro Gly Lys Gly Leu Glu Trp Val Ser
             35                  40                  45

Ala Ile Thr Trp Asn Ser Gly His Ile Asp Tyr Ala Asp Ser Val Glu
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Lys Val Ser Tyr Leu Ser Thr Ala Ser Ser Leu Asp Tyr Trp Gly Gln
                100                 105                 110

Gly Thr Leu Val Thr Val Ser Ser
            115                 120

<210> SEQ ID NO 9
<211> LENGTH: 236
<212> TYPE: PRT
<213> ORGANISM: Artificial Sequence
<220> FEATURE:
<223> OTHER INFORMATION: Antibody

<400> SEQUENCE: 9

Met Asp Phe Gln Val Gln Ile Ile Ser Phe Leu Leu Ile Ser Ala Ser
 1               5                  10                  15

Val Ile Met Ser Arg Gly Asp Ile Gln Met Thr Gln Ser Pro Ser Ser
                 20                  25                  30

Leu Ser Ala Ser Val Gly Asp Arg Val Thr Ile Thr Cys Arg Ala Ser
             35                  40                  45

Gln Gly Ile Arg Asn Tyr Leu Ala Trp Tyr Gln Lys Pro Gly Lys
             50                  55                  60

Ala Pro Lys Leu Leu Ile Tyr Ala Ala Ser Thr Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Val Ala Thr Tyr Tyr Cys Gln Arg
                100                 105                 110

Tyr Asn Arg Ala Pro Tyr Thr Phe Gly Gln Gly Thr Lys Val Glu Ile

```
            115                 120                 125
Lys Arg Thr Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235

<210> SEQ ID NO 10
<211> LENGTH: 470
<212> TYPE: PRT
<213> ORGANISM: Artificial Sequence
<220> FEATURE:
<223> OTHER INFORMATION: Antibody

<400> SEQUENCE: 10

Met Gly Trp Ser Leu Ile Leu Leu Phe Leu Val Ala Val Ala Thr Arg
1               5                   10                  15
Val Leu Ser Glu Val Gln Leu Val Glu Ser Gly Gly Gly Leu Val Gln
            20                  25                  30
Pro Gly Arg Ser Leu Arg Leu Ser Cys Ala Ala Ser Gly Phe Thr Phe
        35                  40                  45
Asp Asp Tyr Ala Met His Trp Val Arg Gln Ala Pro Gly Lys Gly Leu
    50                  55                  60
Glu Trp Val Ser Ala Ile Thr Trp Asn Ser Gly His Ile Asp Tyr Ala
65                  70                  75                  80
Asp Ser Val Glu Gly Arg Phe Thr Ile Ser Arg Asp Asn Ala Lys Asn
                85                  90                  95
Ser Leu Tyr Leu Gln Met Asn Ser Leu Arg Ala Glu Asp Thr Ala Val
            100                 105                 110
Tyr Tyr Cys Ala Lys Val Ser Tyr Leu Ser Thr Ala Ser Ser Leu Asp
        115                 120                 125
Tyr Trp Gly Gln Gly Thr Leu Val Thr Val Ser Ser Ala Ser Thr Lys
    130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
        195                 200                 205
Val Thr Val Pro Ser Ser Ser Leu Gly Thr Gln Thr Tyr Ile Cys Asn
    210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
```

```
                      245                 250                 255
Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465                 470
```